United States Patent [19]

Shofner et al.

[11] 4,017,186
[45] Apr. 12, 1977

[54] ELECTRO-OPTICAL METHOD AND SYSTEM FOR IN SITU MEASUREMENTS OF PARTICULATE MASS DENSITY

[75] Inventors: Frederick M. Shofner; Gerhard Kreikebaum, both of Knoxville, Tenn.

[73] Assignee: Environmental Systems Corporation, Knoxville, Tenn.

[22] Filed: Mar. 5, 1975

[21] Appl. No.: 555,355

[52] U.S. Cl. .............................. 356/103; 250/574
[51] Int. Cl.² ...................................... G01N 21/00
[58] Field of Search .......... 356/102, 103, 104, 207, 356/208; 250/574

[56] References Cited

UNITED STATES PATENTS

| | | | |
|---|---|---|---|
| 3,310,680 | 3/1967 | Hasegawa | 356/104 |
| 3,524,707 | 8/1970 | Hansen, Sr. et al. | 356/207 X |
| 3,563,661 | 2/1971 | Charlson et al. | 356/104 |
| 3,782,824 | 1/1974 | Stoliar | 356/103 |

Primary Examiner—John K. Corbin
Assistant Examiner—Conrad Clark
Attorney, Agent, or Firm—Fitch, Even, Tabin & Luedeka

[57] ABSTRACT

A system and method provides electro-optical in situ measurements of the mass per unit volume of particulate matter suspended in a fluid medium. A beam of electromagnetic radiation is directed through a portion of the medium and radiation back-scattered from an optically defined volume thereof is detected and utilized to provide an indication of the mass of the particles per unit volume of the medium. The beam is preferably a periodically interrupted beam of substantially monochromatic light having a wavelength of the order of magnitude of the mean diameter of the particles of interest. In one embodiment, the d.c. component of the detection signal is filtered out to eliminate the effect of any background radiation.

21 Claims, 4 Drawing Figures

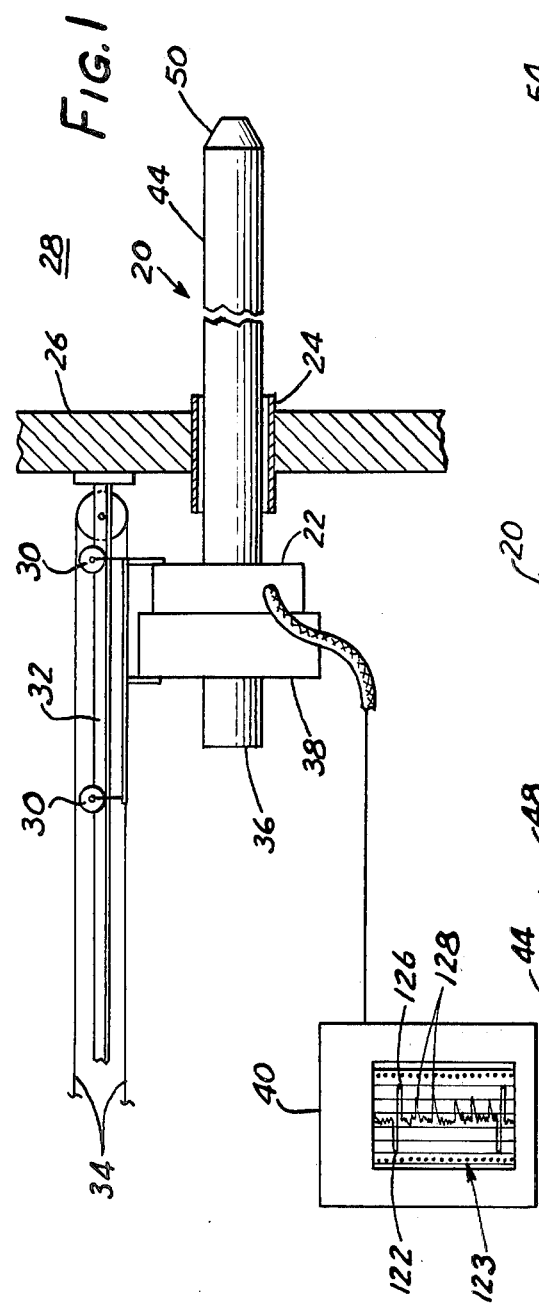
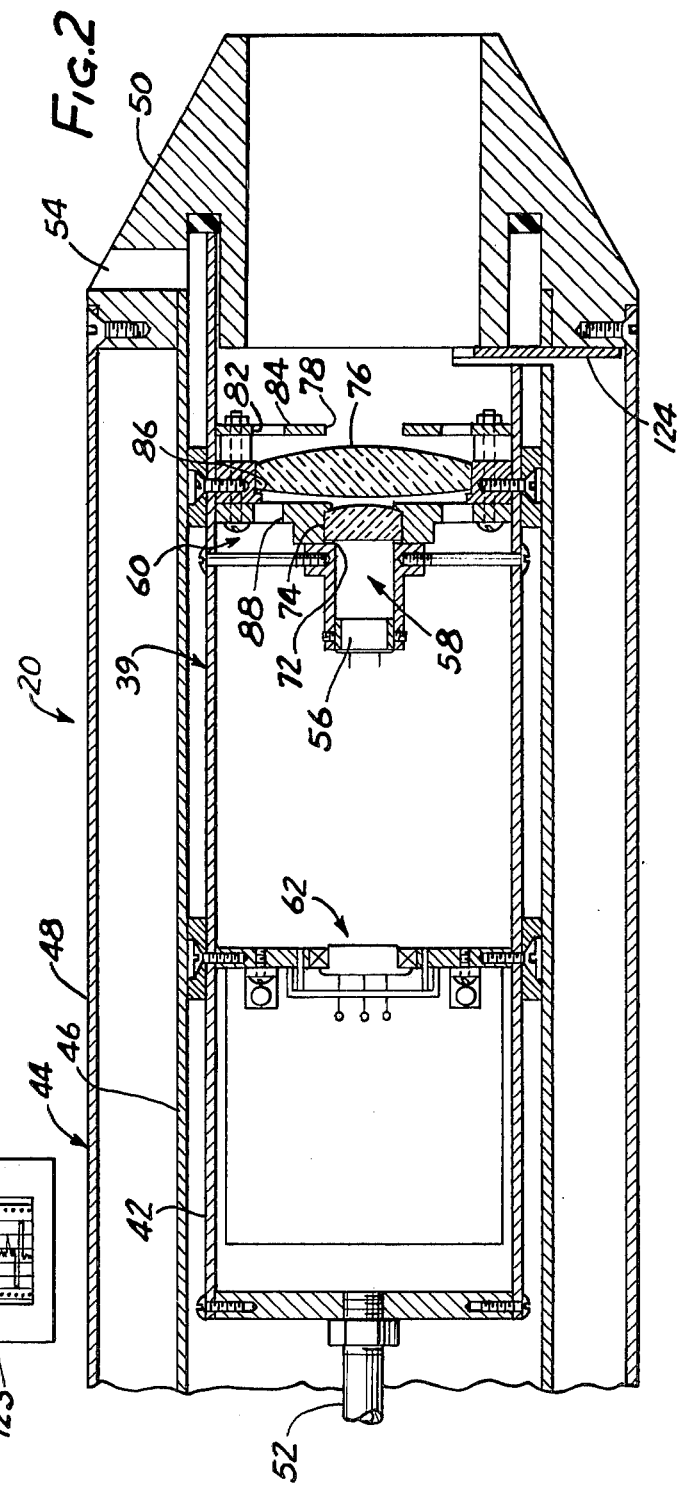

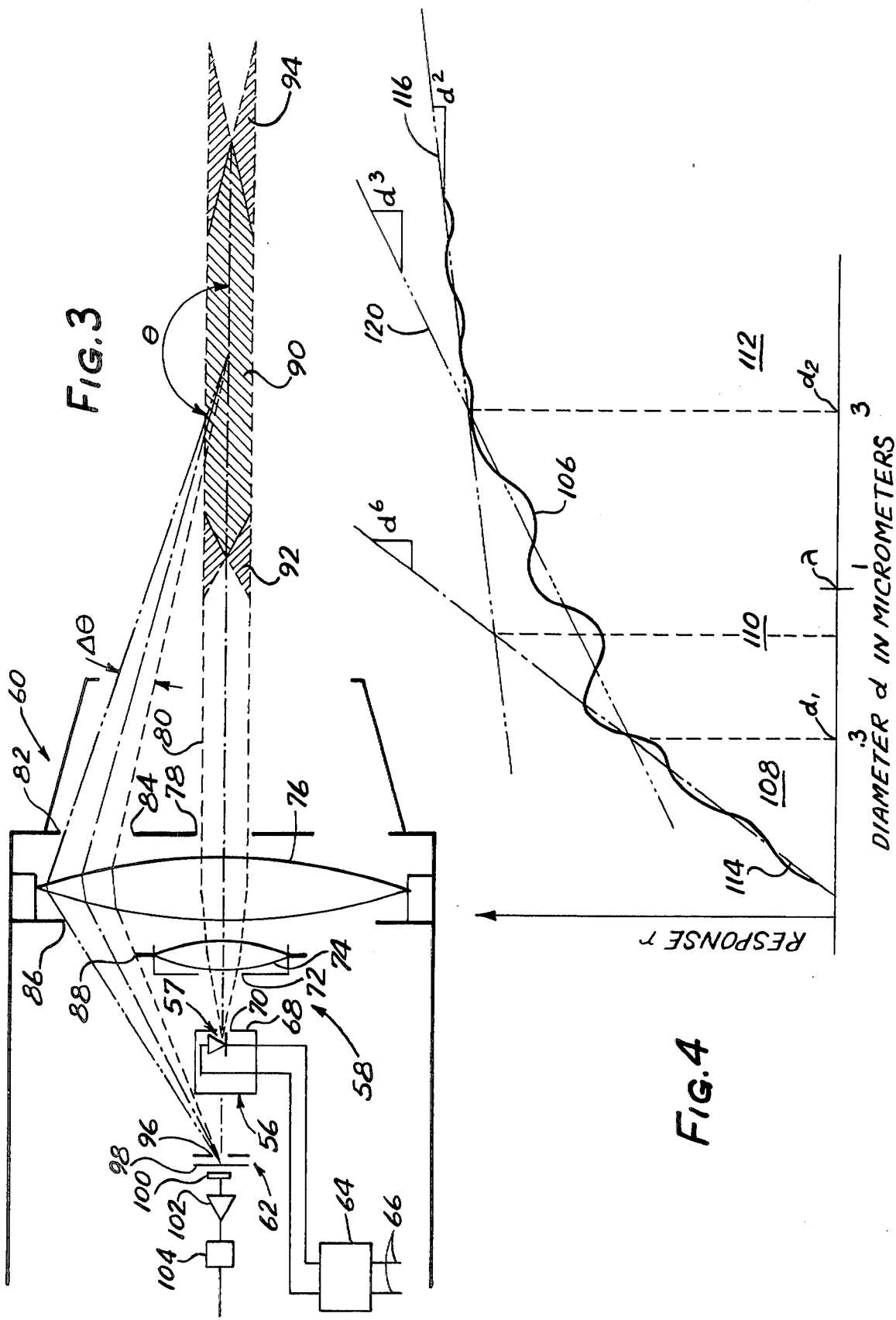

ELECTRO-OPTICAL METHOD AND SYSTEM FOR IN SITU MEASUREMENTS OF PARTICULATE MASS DENSITY

This invention relates generally to electro-optical measurement, in situ, of the mass per unit volume of particles suspended in a fluid medium. More particularly, the invention relates to a method and apparatus where light is directed into a medium containing suspended particles and the intensity of backscattered light is utilized to indicate the mass of the particles per unit volume of the medium.

The mass per unit volume of particulate matter in fluids, and especially in gases, is a basic parameter in respect to particulate mass emission regulations relating to air pollution. It is also an important parameter in respect to the operation of various plants causing pollution, as the mass per unit volume of material going up a stack is an indication of the pollution created as well as an indication of the operating characteristics of a plant or its particulate control equipment, such as electrostatic precipitators or bag-houses. If the process is a combustion process, such as an electricity generating facility, the particulate matter emitted in the process and entrained in the stack gases is an indication of the firing characteristics of the plant. The parameter is also significant in respect to such matters as ground fog near airports and highways.

The most common means for measuring particles contained in such media as stack gases have included such devices as transmissometers, which measure the absorption of light passing through a medium, or mechanical isokinetic sampling trains, which take samples of stack gases and collect particulate matter therein on filters. The former does not provide a true measurement of particle mass density, and the latter does not provide instantaneous measurement.

Therefore, it is an object of the present invention to provide an electro-optical method and apparatus for measuring in situ the mass per unit volume of particles suspended in a fluid medium. It is a further object of the invention to make such measurements utilizing light backscattered by the particles and still more particularly to provide such measurements substantially independent of the sizes of the particles.

Other objects and advantages of the invention will be apparent from the following detailed description, particularly when taken in connection with the appended drawings, in which;

FIG. 1 is a side elevation, partly in section and partly diagrammatical, illustrating apparatus embodying various features of the invention;

FIG. 2 is a cross-sectional view of the sensing head of the apparatus shown in FIG. 1;

FIG. 3 is a diagrammatic illustration of the apparatus shown in FIG. 2, showing optical paths; and FIG. 4 is a typical response curve using the apparatus of the present invention.

The present invention is directed to a system and method for making electro-optical in situ measurements of the mass per unit volume of particulate matter suspended in a fluid medium, such as stack gases. A beam of electromagnetic radiation is directed through a portion of the medium and radiation backscattered from an optically defined volume thereof is detected and utilized to provide an indication of the mass of the particles per unit volume of the medium. The beam is preferably a periodically interrupted beam of monochromatic light having a wavelength of the order of magnitude of the mean diameter of the particles of interest. In one embodiment, the radiation detected is preferably that backscattered at an angle of at least 160° within a range of less than 2°, with radiation being collected substantially equally over a substantial portion of the defined volume and with the d.c. component of the detection signal being filtered out to eliminate the effect of any background radiation.

FIG. 1 shows a preferred form of the invention as utilized for the measurement of the mass of particulate matter per unit volume of a gaseous medium, such as stack gas. More particularly, it illustrates a probe 20 which is rigidly mounted on a chassis 22 for extending through a port 24 in a wall 26 of a duct 28. The chassis 22 is mounted on rollers 30 for rolling on a track 32 in order that the probe 20 may be inserted and withdrawn through the wall 26 and the port 24 and in order that the probe 20 may be moved back and forth across the duct 28 to sense different transverse portions of the duct. A cable 34 may be operated to cause the probe 20 to transverse the duct 28. Also mounted on the chassis 22 are a blower-motor 36 and a filter 38 to supply cool, filtered air to a sensing head 39 mounted within the probe 20. The chassis 22 also contains any necessary connections and electronic circuitry for converting the output of the sensing head 39 into suitable detection signals for operating a recording instrument 40. The chassis 22 may also contain any necessary power supplies and controls for the light source used in the sensing head 39.

As shown in FIG. 2, the sensing head 39 is contained in a casing 42 slidably mounted in a double-walled housing 44 formed of walls 46 and 48 and terminating in a nose piece 50. A rod 52 is utilized to insert the sensing head 39 into the housing 44 and to withdraw it therefrom. It may be hollow to accommodate connecting wires. Withdrawal of the head may be to protect it from a particularly hostile environment or to permit calibration of the device, as will be described in greater detail below. The space between the walls 46 and 48 of the housing 44 serves as a dead air space or is filled with insulation to provide for temperature control for the sensing head. The space between the walls 42 and 46 defines a channel through which the cool, filtered air is driven by the blower 36 may be passed along the exterior of the sensing head 39 to protect the sensing head from high temperatures. This air exits through a port 54 downstream of the sensing head. A small part of the air is passed out the center of the nose piece 50 to keep contaminants out and to keep the front end of the sensing head relatively cool. The rate of air flow desired depends upon the environment to which the sensing head is exposed; however, it is important that the amount of air expelled through the open end of the nose piece 50 not be so great as to perturb to any great degree the environment being measured.

The sensing head 39 as shown in FIG. 2, is substantially circularly symmetrical. It may be noted that all of the necessary conducting wires are not shown, for the sake of ease of understanding the drawings. It should also be noted that the various means for mounting the various pieces to the casing 42 are of small area relative to the total area so as not to present substantial overall obstructions to the passage of light.

Although FIG. 2 shows an actual layout of a functioning sensing head 39, it will be somewhat easier to understand the operation of the device by reference to the more diagrammatic illustration of the same parts in FIG. 3. As illustrated in FIG. 3, the sensing head 39 includes a light source 56, which may be a light emitting diode 57, with optical means 58 for directing light from the light source 56 into the gaseous medium in the duct 28, optical means 60 for collecting the light backscattered from the medium, and a light detector 62 for sensing the collected backscattered light and converting it into a detection signal. Electronics may be contained in the head 39.

The light emitting diode 57 may be operated continuously or caused to emit light periodically under the control of a pulser 64 which may receive power from a conventional source over conductors 66. A suitable pulse rate is 1000 Hz. The light source 56 has a light tight housing 68 with an aperture 70 through which the light is emitted. This light passes through an aperture 72 into a collimating lens 74, thence through a collecting lens 76 and an aperture 78. The effect of these lenses and apertures is to form a substantially collimated beam of light 80 exiting through the open nose piece 50 into the environment in which the measurement is to be made. These apertures and lenses comprise the optical means 58 for directing the beam into the medium. This beam is preferably circular and of substantially uniform intensity across the beam. Further, the pulses of light are made substantially uniform in intensity. For the purposes of this explanation, it will be assumed that the absorption and scattering of light as the beam 80 traverses the medium does not produce a substantial diminution in the beam over the portion of the medium where the measurement is to be made. Some diminution can obviously be tolerated without substantial error, and sometimes substantial diminution is of no great consequence, for example, in certain high particle density situations. It will also be assumed in this explanation that multiple scattering of the light is inconsequential, for it is inconsequential in many practical instances.

Light striking particulate matter suspended in the medium is scattered in all directions. In the device illustrated in FIGS. 1–3, it is the light backscattered through the open nose piece 50 that is of interest. This returning light is collected by the outer portion of the collecting lens 76 and directed to the light detector 62. Masks 82, 84, 86 and 88 define annular apertures for limiting the direction whence light can reach the detector 62. The consequence of this is that the only light sensed is that arising in the acceptance angle of the optical means 60, which comprises the outer portion of the collecting lens 76 and the respective apertures. Neglecting background light and other extraneous agencies, the only light in the system is that scattered from the beam 80. Hence, light reaching the detector 62 is only that light arising in the volume defined by the intersection of the beam 80 with the solid acceptance angle of the optical means 60, as illustrated by the shaded portions 90, 92 and 94 shown in FIG. 3. It is evident that the volumes 92 and 94 are penumbral in nature, as light from these regions cannot pass through all portions of the optical means 60 to reach the detector 62. Therefore, the region 90 may be considered the effective sampling volume; that is, it is the limited volume of that part of the medium traversed by the beam 80, to which the sensing head 39 is most sensitive. For the purposes of this invention, substantially all radiation backscattered from particles disposed within the sampling volume (i.e. region 90) is potentially detectable. From a practical standpoint, including physical design of the apparatus, in the preferred embodiment of the invention, it is light backscattered at a scattering angle $\theta$ of between about 100° and about 175° that is detected. Within this range, preferably there is chosen a relatively narrow angular range $\Delta\theta$, e.g. 2°–5°, of backscattered radiation detectable by the detector 62. In one embodiment a scattering angle $\theta$ of at least 160° within an angular range $\Delta\theta$ of about 2° has proven effective in measuring particle density.

The light detector 62 may comprise a detector aperture 96, a detector filter 98 and a photosensitive device 100. The photosensitive device may be a conventional photodetector for converting light striking its photosensitive medium into detection signals which may be amplified by an amplifier 102 and further processed by processing circuitry 104, to produce a signal suitable for recording on the recorder 40. The amplifier, or the processing circuitry, preferably includes a filter, which may be a simple capacitor, for eliminating any d.c. component from the detection signal. When using a pulsed light source, such d.c. component is occasioned by background radiation. Hence, its elimination serves to eliminate the effect of background light, thereby producing a detection signal truly dependent upon pulsed light from the source.

Before considering the operation of the apparatus as a device for determining mass per unit volume, an additional useful (but not essential) feature of the optical system should be noted. As some portions of the sampling region 90 are nearer to the sensing head than others, the system would normally be preferentially sensitive to the nearer parts of the region. However, this need not be the case, if the angular range $\Delta\theta$, that is, the range of backscattering angle within which light may reach the photodetector 62, is held constant along the beam. This may be achieved by providing a limited sensing area for the detector 62. Laws of optics require that as a source point is moved toward a convex lens, the image point on the other side of the lens moves away from the lens. The detailed and practical consequences of this law are that if light collected from particles in the central part of the sampling region 90 is "focused" on the detector 62, light collected from the nearer and farther portions of the sampling region will be "out of focus" at the detector and some of the light will miss the photosensitive surface and not be detected. This effect both compensates the angular range received, making it constant in the optical part of the sampling region, and truncates or "cuts-off" reception at the near and far extremities of the sampling region, thus optically defining the sampling volume (in conjunction with the above-described beam definition).

Under certain conditions, the detection signal of the apparatus as thus described is a true and direct measure in situ of the mass per unit volume of the particles suspended in the gaseous medium in the duct 28. This parameter may be considered mass density, provided that this is understood to be the density of the particles in their suspending medium, and not the density of the particles themselves. The parameter is more commonly referred to as mass concentration. To the extent that the conditions of the described embodiment are not satisfied, the measurement is less accurate. However, it has utility for many practical measurements where the conditions obtain relatively closely and in many instances where exact quantitative measurements are not needed.

The basis for the direct relationship between mass per unit volume and backscattered radiation in the present invention is described by Mie scattering theory. This phenomenon is illustrated in FIG. 4 where a curve 106 on a log-log scale represents the detection signal $r$ corresponding to the intensity of backscattered light from a single particle, as measured at the detector 62, as a function of particle diameter $d$, using monochromatic light of wavelength $\lambda$. The particular curve shown is for water, which has a refractive index of 1.33, at a backscattering angle $\theta$ of about 175° and an angular range $\Delta\theta$ of about 1°, with a wavelength $\lambda$ of about $0.9\mu$. The diameter $d$ is given is micrometers.

The curve 106 is a fundamental theoretically and experimentally established curve. It may be noted that there are three distinct regions to the curve, indicated as 108, 110 and 112. In the region 108 of very small particle sizes, the curve 106 approaches an asymtote 114. This is the region of Rayleigh scattering, where light is scattered by very small particles in a manner dependent upon $d^6$. In the region 112 an asymtote 116 is approached by the curve 106 at very large particle sizes, where light is scattered according to classical geometric principles in a manner dependent upon $d^2$, i.e., upon the cross-sectional area of the particle. It may be noted that the curve 106 lies relatively close to the asymtote 114 below about $0.3\mu$ or $\lambda/3$ and relatively close to the asymtote 116 above about $3\mu$ or $3\lambda$. In the region 110 the curve 106 lies relatively close to an average line 120 which follows a $d^3$ dependence. This is the region of interest in the present invention.

The curve 106 is fraught with significance to the present invention, even when, and indeed particularly when, the specific conditions pertaining to the particular curve shown are made more general and applicable to conditions found in actual practical measurements. Within practical limits, dependence of the curve on index of refraction, angle of backscattering $\theta$, and angular range $\Delta\theta$ is small. The intersection of the asymtotes is at a diameter $d$ less than or approximately equal to the wavelength $\lambda$ of the incident light, with the wavelength $\lambda$ at approximately the geometric mean of the range of Mie scattering. In practical circumstances, the particles are of different sizes over a range of significance, are not perfectly spherical, and have somewhat different surface characteristics, as the index of refraction. This results in smoothing of the response curve 106, whereby under actual circumstances the curve 106 averaged over many varied particles, approaches the average line 120, which truly represents a $d^3$ dependence. As the backscattering angle $\theta$ increases from 90° toward 180°, there is a broadening of the range of particle sizes over which such $d^3$ dependence is valid.

To elaborate, as a particle of a given size, say $1\mu$ for this example, is moved around within the sampling volume, the characteristic curve will slightly shift such that when the contributions of many $1\mu$ particles throughout the sampling volume are considered, those which contribute relatively more radiation that the $d^3$ average response will be balanced negatively by those which contribute relatively less radiation due to shifts in the characteristic curve. Additionally, if the particle is not spherical but is elongated in one dimension, or is irregular, or has non-uniform surface characteristics, then this will also shift the characteristic curve such that the plurality of these particles will yield a response that is closer to the $d^3$ average response than to the idealized characteristic curve for a single spherical particle of uniform composition at a single point in the sampling volume. For non-spherical particles, the diameter $d$ is the mean diameter of the particles. Still further, as a practical matter one is rarely interested in the measurement of a plurality of particles of a single size of uniform composition; rather one is almost always concerned with the measurement of a distribution of particle sizes. The total result of all these "averaging effects in practical situations is that the method and apparatus of the invention herein described follows very nearly a $d^3$ response characteristic.

Having established the basis of the $d^3$ characteristic, it is instructive to consider an elementary example elucidating the importance of this response characteristic. Suppose two classes of spherical particles having diameters $d_a$ and $d_b$, respectively, the same composition or, more specifically, the same index of refraction $\hat{m} = m_1 - jm_2$, and the same density $\rho$. Now, from the above explanation, the average single particle response $\bar{r}$ may be described as $$\bar{r} = Kd^3,\ d_1 < d < d_2 \quad (1)$$

where $d_1$ and $d_2$ are the limits of $d^3$ dependence, and $K$ is a constant. The integrated output $R_a$ for $N_a$ particles/unit volume of a diameter $d_a$ in a total sampling volume V is therefore $$R_a = N_a\ V\ Kd_a^3. \quad (2)$$

Further, the mass/unit volume $X_a$ is given, for particles all having the same size $d_a$, by $$X_a = N_a\ \pi/6\ d_a^3\rho. \quad (3)$$

The same relationships obtain for particles of diameter $d_2$.

$$R_b = N_b\ V\ K\ d_b^3. \quad (4)$$

$$X_b = N_b(\pi/6)d_b^3\rho \quad (5)$$

Dividing Equation (2) by Equation (4), $$\frac{R_a}{R_b} = \frac{d_a^3}{d_b^3}\ \frac{N_a}{N_b}. \quad (6)$$

Dividing Equation (3) by Equation (5), $$\frac{X_a}{X_b} = \frac{d_a^3}{d_b^3}\ \frac{N_a}{N_b}. \quad (7)$$

Hence, $$\frac{R_a}{R_b} = \frac{X_a}{X_b}. \quad (8)$$

This demonstrates that, within the established limits, $d_1 < d < d_2$, the output signal in respect to a given mass per unit volume of particles of respective sizes is independent of the sizes of the particles. The signal is thus truly indicative of the mass per unit volume of particles of that size. The total or integrated output signal $R$ for all particles within the range $d_1 < d < d_2$, is therefore truly indicative of the mass per unit volume of all such particles, $$R = CX \qquad (9)$$

where $C$ is a constant.

Thus, if the mass of $3\mu$ particles is equal to that of $0.3\mu$ particles in a particular medium, the output signals are identical, even though the number of particles differs by $10^3$. This is clearly the requirement placed upon an instrument which responds to mass per unit volume.

The limits of $d_1 < d < d_2$ is about an order of magnitude with the wavelength $\lambda$ at about the geometric mean of the extremes of the range. Within this range, the measurement made with the described apparatus very accurately indicates mass per unit volume. In many practical situations, the effective range may extend even further. For example, most of the mass of interest will often be confined to an order of magnitude range in particle size or less. Thus, even though the response is not truly $d^3$ outside this range, the errors caused are nominal. This is particularly true in view of the small contributions to mass generally found for submicron particles in many industrial processes. On the other side, the large particles, those above $3\mu$, either may made but a small fractional contribution or may not be of interest to the measurement. In such circumstances the weighting provided by the apparatus may, in fact, be preferable for monitoring purposes.

The example thus described will produce an accurate measure of mass per unit volume of particulate matter suspended in a fluid medium where the mean diameters of the particles are of about the same order of magnitude as the wavelength of the monochromatic light source, which is $0.9\mu$ in the example. Such light is available from gallium arsenide light emitting diodes or lasers.

It is a matter of design to change the range of diameters of interest simply by changing the wavelength of the source radiation. Thus, as a simple example, if one wished to make measurements wherein true mass density response was achieved between $1\mu$ and $10\mu$, one would choose a source radiation in the vicinity of $3\mu$. The net effect is to shift all of the curves of FIG. 4 horizontally. Of course, the curves are shifted vertically upward by increasing such things as radiation source power, detector response and amplifier gain.

Various modifications may be made in the preferred embodiment of the present invention as described above without departing from the scope of the invention. For example, the optical arrangement may be different, as may be desirable for certain measurements. Different scattering angles and angular ranges may be used. Other light sources, including filtered incandescent lamps, may be used. Depending upon the accuracy requirements of the measurement, the apparatus may be used in various environments and over a wider range of particle sizes. The bandwidth of the substantially monochromatic light may be considerable, as this also tends to average out the response curve to approach the $d^3$ relationship. For the purposes of the present invention, a monochromatic light source or source of monochromatic electromagnetic radiation may be defined as a source of electromagnetic radiation where a major portion of the electromagnetic radiation that is within the effective range of sensitivity of the detector 62 is within a relatively narrow bandwidth.

A bandwidth of 200 angstroms for a gallium arsenide light emitting diode has been found suitable, operating at a power of 5 to 10 mw. and pulsed at a frequency of about 1000 hz.

Means may be provided for automatic or manual calibration of the apparatus. To this end, the light source may be turned off or the returning light may be blocked and the recorder 40 may be adjusted, as is conventional with recorders, to indicate zero mass per unit volume, i.e., absence of backscattering particles, as shown at 122 on the recorder chart 123. The sensing head 39 may be partly withdrawn from the housing 44 by the rod 52 to a calibration position and a standard scattering plate 124 may be remotely positioned, as by a rod extending along the space between the walls 46 and 48, to lie in the beam 80 to provide a standard backscattering of light. The recorder 40 is then adjusted to a standard calibrated position, such as full scale, shown at 126. The device is thereby calibrated so that the intermediate readings accurately indicate mass per unit volume, relative to the standard 124.

The apparatus may be utilized for in situ measurements in various environments. The recorder output illustrated in FIG. 1 is typical of measurements in a stack following an electrostatic precipitator which is rapped periodically to knock accumulated particles from the plates of the precipitator into a receptacle. The periodic rapping produces the peaks 128 on the recorder chart 123.

What is claimed is:

1. A system for measuring in situ the mass per unit volume of particles suspended in a fluid medium, said system comprising a source of substantially monochromatic electromagnetic radiation having a wavelength of the order of magnitude of the mean diameter of each of a majority of the particles of interest, means for directing a beam of radiation from said source through a portion of said medium, photodetector means having a photosensitive medium for producing electronic detection signals systematically related to the intensity of electromagnetic radiation falling on said photosensitive medium, said photosensitive medium being located out of the path of said beam, optical means for directing upon said photosensitive medium electromagnetic radiation backscattered from a distally and proximally optically limited region of the portion of said fluid medium traversed by said beam, which limited region contains many of said particles, and indicator means responsive to said electronic detection signals for indicating the mass of said particles per unit volume of the fluid medium substantially independently of the size of particles of mean diameters of the order of magnitude of the wavelength of the radiation from said source.

2. A system according to claim 1 wherein said optical means includes a narrow band pass filter passing electromagnetic radiation of the frequency of said monochromatic radiation.

3. A system according to claim 1 wherein said source is a laser.

4. A system according to claim 1 wherein said source is a light emitting diode.

5. A system according to claim 1 wherein the wavelength of said monochromatic radiation is less than about the geometric mean of the extremes of the range of the mean diameters of the particles of interest.

6. A system according to claim 1 wherein said means for directing includes means for collimating said beam, and said optical means includes means for collecting electromagnetic radiation substantially equally over a substantial part of said region.

7. A system according to claim 1 wherein said optical means collects electromagnetic radiation backscattered at least about 160°.

8. A system according to claim 7 wherein said optical means collects electromagnetic radiation backscattered within a range of less than about 2°.

9. A system according to claim 1 including means for substantially interrupting said beam periodically, and wherein said indicator means includes filter means for eliminating any d.c. component of said detection signals, thereby eliminating the effect of background radiation.

10. A system according to claim 1 wherein said optical means includes a collection system for collecting backscattered radiation symmetrically around said beam.

11. A system according to claim 10 wherein said collection system includes an optical lens for receiving radiation concentrically of said beam and directing the radiation on said photosensitive medium, said photosensitive medium being disposed coaxially of said beam on the opposite side of said source.

12. A system for measuring in situ the mass per unit volume of particles suspended in a fluid medium, said system comprising a source of substantially monochromatic electromagnetic radiation having a wavelength of about the geometric mean of the extremes of the range of the mean diameters of the particles of interest, means for directing a collimated beam of radiation from said source through a portion of said medium, photodetector means having a photosensitive medium for producing electronic detection signals systematically related to the intensity of electromagnetic radiation falling on said photosensitive medium, said photosensitive medium being located out of said beam, optical means for directing upon said photosensitive medium electromagnetic radiation backscattered from a distally and proximally optically limited region of the portion of said fluid medium traversed by said beam, which limited region has volume to contain many of said particles, and means responsive to said detection signals for indicating the mass of said particles per unit volume of the fluid substantially independently of the size of particles of mean diameters of the order of magnitude of the wavelength of the radiation from said source.

13. A system for measuring in situ the mass per unit volume of particles suspended in a fluid medium, said system comprising a source of substantially monochromatic electromagnetic radiation having a wavelength of the order of magnitude of the mean diameter of each of a majority of the particles of interest and less than about the geometric means of the extremes of the range of the mean diameters of said particles of interest, means for directing a collimated beam of radiation from said source through a portion of said medium, means for interrupting said beam periodically, photodetector means having a photosensitive medium for producing eletronic detection signals systematically related to the intensity of electromagnetic radiation falling on said photosensitive medium, siad photosensitive medium being located out of the path of said beam, optical means for directing upon said photosensitive medium electromagnetic radiation backscattered at least about 160° within a range of less than about 2° from a distally and proximally optically limited region of the portion of said fluid medium traversed by said beam, which limited region has volume to contain many of said particles, said optical means including means for collecting electromagnetic radiation substantially equally over a substantial part of said region, and indicator means responsive to said electronic detection signals for indicating the mass of said particles per unit volume of the fluid medium substantially independently of the size of particles of mean diameters of the order of magnitude of the wavelength of the radiation from said source, said indicator means including filter means for eliminating any d.c. component of said detection signals, thereby eliminating the effect of background radiation.

14. A method for measuring in situ the mass per unit volume of particles suspended in a fluid medium, said method comprising directing a beam of substantially monochromatic electromagnetic radiation through a portion of said medium, the wavelength of said radiation being of the order of magnitude of the mean diameter of each of a majority of the particles of interest, detecting the intensity of radiation backscattered by such particles in a distally and proximally optically limited region of the portion of said medium illuminated be said beam to produce detection signals systematically related to said intensity, said limited region containing many suspended particles, and utilizing said detection signals to provide an indication of the mass of said particles per unit volume of the medium substantially independently of the size of particles of mean diameters of the order of magnitude of the wavelength of the radiation from said source.

15. A method according to claim 14 wherein said monochromatic radiation is generated at a wavelength less than about the geometric mean of the extremes of the range of mean diameters of the particles of interest.

16. A method according to claim 14 wherein most of the backscattered electromagnetic radiation detected has been backscattered at least about 160°.

17. A method according to claim 16 wherein the backscattered electromagnetic radiation detected has been backscattered within a range of less than about 2°.

18. A method according to claim 14 wherein said beam is periodically substantially interrupted, and any d.c. component of said detection signals is filtered out, thereby eliminating the effect of background radiation.

19. A method according to claim 14 wherein said beam is a collimated beam and the radiation is detected substantially equally over a substantial part of said region.

20. A system according to claim 1 including calibration means comprising means operative during calibration for interrupting radiation backscattered from said region upon said photosensitive medium, thereby producing a zero reference indication by said indicator means, a standard scattering medium movable into said beam during calibration to backscatter a standard radiation intensity to said photosensitive medium, thereby calibrating the response of said indicator means relative to such standard intensity.

21. A method according to claim 14 wherein said measuring is calibrated by interrupting backscattered radiation being detected to provide a zero reference, and alternately disposing a standard scattering medium in said beam to backscatter a standard radiation intensity for detection, whereby the indication of the mass of said particles per unit volume of the medium is made relative to such standard intensity.

* * * * *

UNITED STATES PATENT AND TRADEMARK OFFICE
CERTIFICATE OF CORRECTION

PATENT NO. : 4,017,186
DATED : April 12, 1977
INVENTOR(S) : Frederick M. Shofner, et al.

It is certified that error appears in the above-identified patent and that said Letters Patent are hereby corrected as shown below:

Column 1, line 50, change ";" to --:--.

Column 2, line 23, change "transverse" to --traverse--.

Column 4, line 62, after "density" insert --$\rho$--.

Column 5, line 15, change "is", second occurrence, to --in--.

Column 6, line 10, after "averaging", insert a quotation mark.

Column 6, line 39, change "$\underline{d}_2$" to --$\underline{d}_b$--.

Column 7, line 27, change "made" to --make--.

Column 9, Claim 13, line 55, change "means" to --mean--.

Column 9, Claim 13, line 63, change "siad" to --said--.

Column 10, Claim 14, line 25, change "be" to --by--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks